United States Patent
Shmulewitz et al.

(10) Patent No.: US 6,569,145 B1
(45) Date of Patent: May 27, 2003

(54) PRESSURE-CONTROLLED CONTINUOUS CORONARY SINUS OCCLUSION DEVICE AND METHODS OF USE

(75) Inventors: Ascher Shmulewitz, Mercer Island, WA (US); Robert S. Bley, Menlo Park, CA (US); Robert L. Wilcox, Bothell, WA (US)

(73) Assignee: TransVascular, Inc., Menlo Park, CA (US)

( * ) Notice: Subject to any disclaimer, the term of this patent is extended or adjusted under 35 U.S.C. 154(b) by 0 days.

(21) Appl. No.: 09/275,797

(22) Filed: Mar. 25, 1999

(51) Int. Cl.$^7$ ............................................. A61M 31/00
(52) U.S. Cl. .................. 604/509; 604/102.01; 604/523
(58) Field of Search ................................ 604/500, 506, 604/507, 508, 509, 523, 6.16, 8, 9, 93.01, 96.01, 99.04, 102.01, 102.02, 102.03, 104, 264, 907, 912, 914, 915–21

(56) References Cited

U.S. PATENT DOCUMENTS

| | | | |
|---|---|---|---|
| 3,833,003 A | | 9/1974 | Taricco ......................... 128/347 |
| 4,459,977 A | | 7/1984 | Pizon et al. ................. 128/1 D |
| 4,648,384 A | | 3/1987 | Schmukler ................. 128/1 D |
| 4,689,041 A | | 8/1987 | Corday et al. ................. 604/53 |
| 4,771,777 A | * | 9/1988 | Horzewski et al. .......... 128/344 |
| 4,850,969 A | * | 7/1989 | Jackson ......................... 604/96 |
| 4,934,996 A | | 6/1990 | Mohl et al. .................... 600/17 |
| 4,943,277 A | | 7/1990 | Bolling ........................ 604/96 |
| 4,969,470 A | | 11/1990 | Mohl et al. .................. 128/673 |
| 5,024,668 A | | 6/1991 | Peters et al. ................. 606/194 |
| 5,147,332 A | * | 9/1992 | Moorehead ................... 604/247 |
| 5,180,364 A | * | 1/1993 | Ginsberg ....................... 604/53 |
| 5,224,938 A | * | 7/1993 | Fenton, Jr. ................... 604/247 |
| 5,395,331 A | | 3/1995 | O'Neill et al. ................. 604/96 |
| 5,533,957 A | | 7/1996 | Aldea ........................... 600/16 |
| 5,916,193 A | * | 6/1999 | Stevens et al. ................ 604/53 |
| 6,007,479 A | * | 12/1999 | Rottenberg et al. ........... 600/16 |

OTHER PUBLICATIONS

Aldea, G.S. et al., "Salvage of Ischemic Myocardium With Simplified and Even Delayed Coronary Sinus Retroperfusion," *The Annals of Thoracic Surgery*, 62(1):9–15 (1996).
Aldea, G.S. et al., "Heterogeneous Delivery of Cardioplegic Solution in the Absence of Coronary Artery Disease," *J. of Thoracic and Cardiovascular Surgery*, 99:345–353 (1990).
Beyersdorf, F. et al., "Studies on Prolonged Acute Regional Ischemia," *J. of Thoracic and Cardiovascular Surgery*, 98:112–126 (1989).
Bolling, S.F. et al., "Improved Myocardial Preservation During Global Ischemia by Continuous Retrograde Coronary Sinus Perfusion," *J. of Thoracic and Cardiovascular Surgery*, 86:659–666 (1983).
Fedele, F.A. et al., "Effect of Pressure–controlled Intermittent Coronary Sinus Occlusion on Pacing–induced Myocardial Ischemia in Domestic Swine," *Circulation*, 77(6):1403–1413 (1988).

(List continued on next page.)

*Primary Examiner*—Sharon Kennedy
*Assistant Examiner*—Catherine Serke
(74) *Attorney, Agent, or Firm*—Robert D. Buyan; Stout, Uxa, Buyan, Mullins, LLP

(57) ABSTRACT

Apparatus and methods for perfusing ischemic myocardium are provided using a tubular member having an end region adapted to be disposed in a portion of a patient's venous vasculature. The end region includes a lumen and a valve in communication with the lumen that controls pressure within an occluded portion of the vasculature by venting excess blood at a location proximal of a point of occlusion of the vasculature via the valve. An occlusion element optionally may be provided in the end region that retains the tubular member within the patient's venous vasculature and occludes the flow of blow around the lumen.

5 Claims, 4 Drawing Sheets

OTHER PUBLICATIONS

Kar, S. et al., "Synchronized Coronary Venous Restroperfusion for Support and Salvage of Ischemic Myocardium During Elective and Failed Angioplasty," *J. American College of Cardiology*, 18:271–282 (1991).

Lazar, H.L. et al., "Reversal of Reperfusion Injury After Ischemic Arrest with Pressure–controlled Intermittent Coronary Sinus Occlusion," *J. of Thoracic and Cardiovascular Surgery*, 95:637–642 (1988).

Lazar, H.L. et al., "Myocardial Energy Replenishment and Reversal of Ischemic Damage by Substrate Enhancement of Secondary Blood Cardioplegia with Amino Acids during Reperfusion," *J. Thoracic and Cardiovascular Surgery*, 80:350–359 (1980).

Menasche, P. et al., "Cardioplegia by Way of the Coronary Sinus for Valvular and Coronary Surgery," *J. American College of Cardiology*, 18(2):628–636 (1991).

Partington, M.T. et al., "Studies of Retrograde Cardioplegia," *J. of Thoracic and Cardiovascular Surgery*, 97:613–622 (1989).

Partington, M.T. et al., "Studies of Retrograde Cardioplegia," *J. of Thoracic and Cardiovascular Surgery*, 97:605–612 (1989).

Rydén, L. et al., "Pharmacokinetic Analysis of Coronary Venous Retroinfusion: A Comparison With Anterograde Coronary Artery Drug Administration Using Metoprolol as a Tracer," *J. American College of Cardiology*, 18(2):603–612 (1991).

Schaper, J. et al., "Ultrastructural Study Comparing the Efficacy of Five Different Methods of Intraoperative Myocardial Protection in the Human Heart," *J. of Thoracic and Cardiovascular Surgery*, 92:47–55 (1986).

Stirling, M.C. et al., "Distribution of Cardioplegic Solution Infused Antegradely and Retrogradely in Normal Canine Hearts," *J. of Thoracic and Cardiovascular Surgery*, 98:1066–1076 (1989).

\* cited by examiner

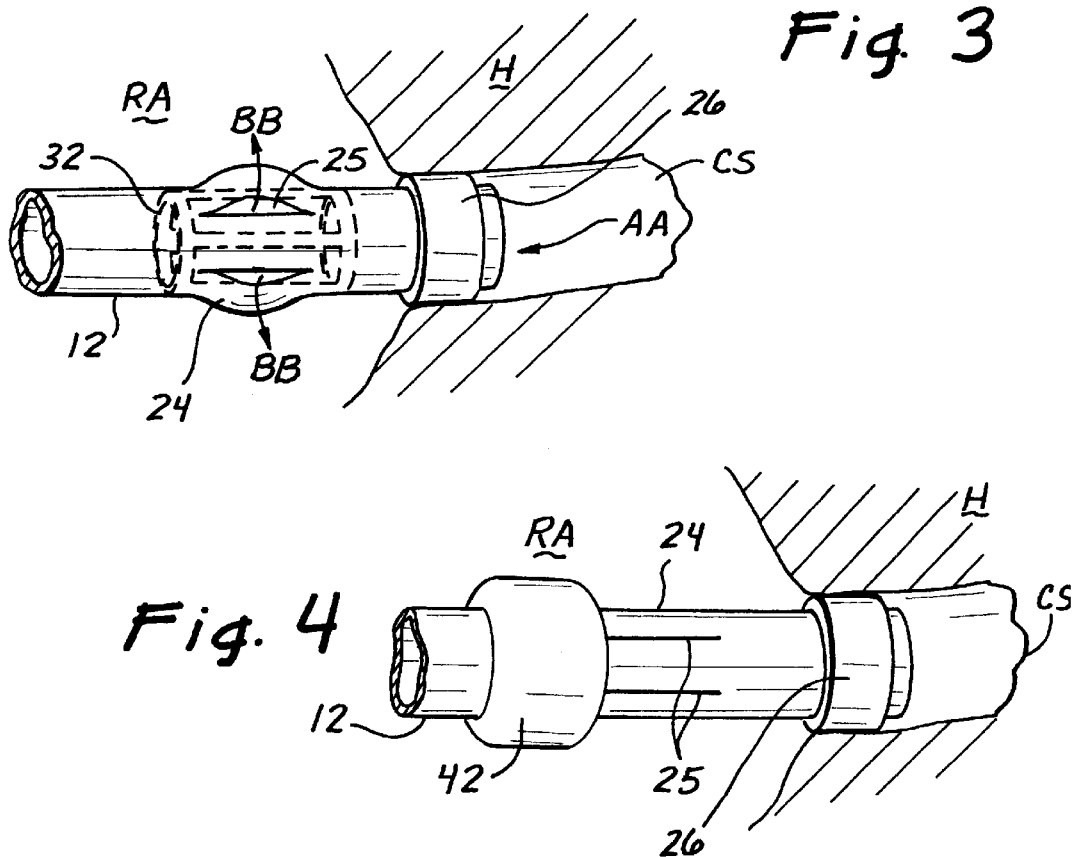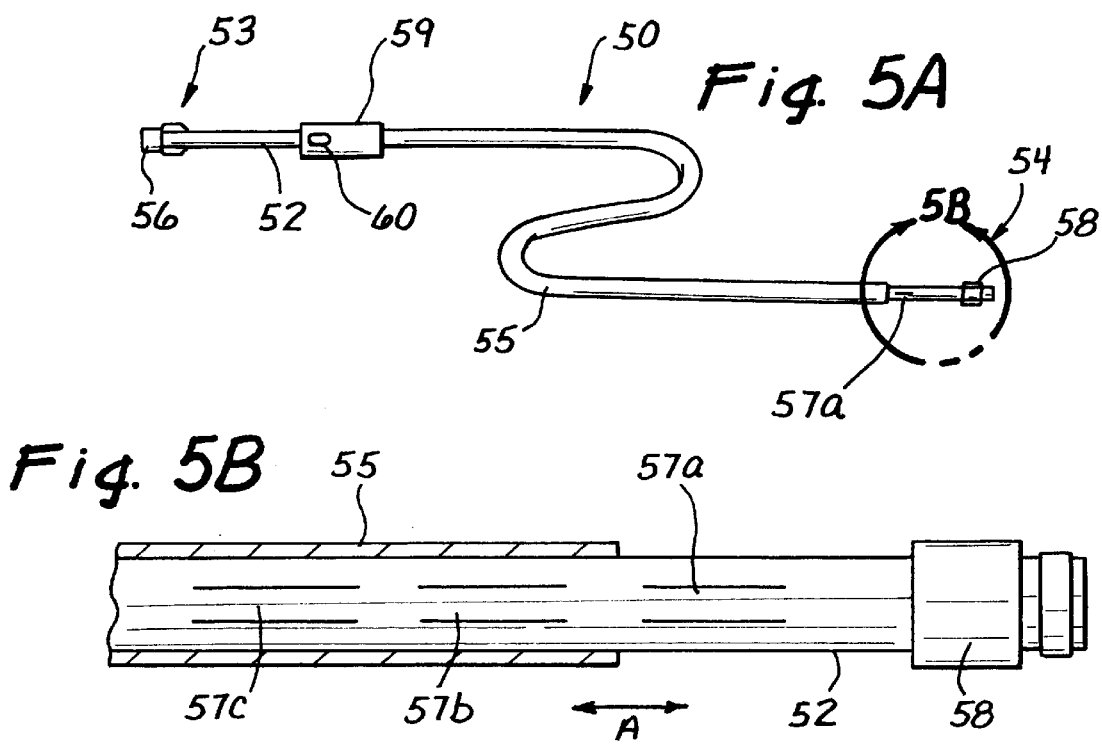

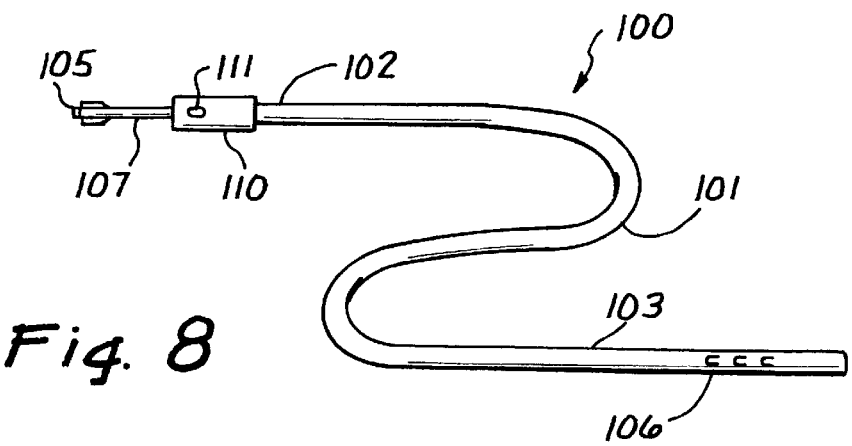
Fig. 8
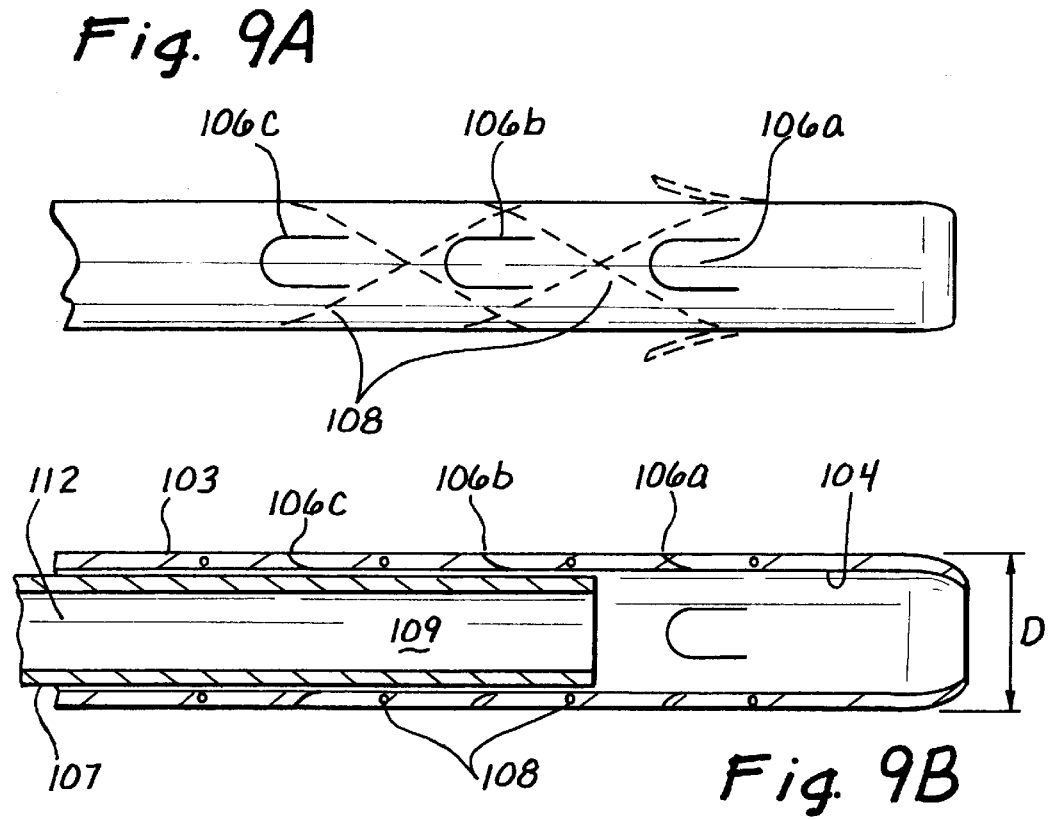
Fig. 9A
Fig. 9B
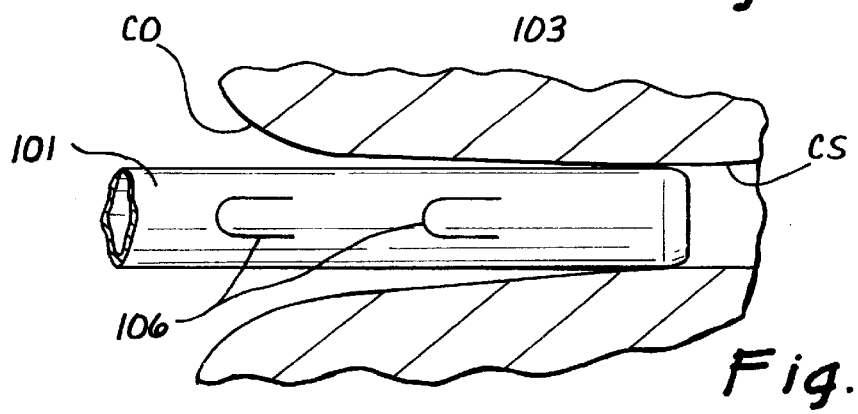
Fig. 10

PRESSURE-CONTROLLED CONTINUOUS CORONARY SINUS OCCLUSION DEVICE AND METHODS OF USE

FIELD OF THE INVENTION

The present invention relates to apparatus and methods for treating ischemic heart disease. In particular, the present invention relates to apparatus and methods that occlude a portion of the venous vasculature to perfuse the myocardium with blood from the venous system.

BACKGROUND OF THE INVENTION

The cardiac perfusion system is composed of the left and right coronary arteries, which perfuse the myocardium from the epicardial surface to the endocardium. Blood flows through the capillaries to the coronary veins, and into the right atrium via the coronary sinus. Two additional systems, the lymphatic and the Thebesian veins, drain a portion of the blood perfused into the myocardium directly into the heart chambers. The venous system has extensive collaterals and, unlike the coronary arteries, does not occlude in atherosclerotic disease.

Atherosclerosis is a primary cause of myocardial ischemia. A number of techniques have been developed to treat atherosclerotic ischemic heart disease. These treatments have improved the lives of millions of patients worldwide, yet for certain classes of patients current technology offers little relief or hope.

Best known of the current techniques is coronary artery bypass grafting, wherein an incision is made to expose the patient's heart, and one or more coronary arteries are replaced with saphenous veins. Conventional open heart surgery, however, is time-consuming and costly, involves a significant risk of mortality, requires a lengthy period of recuperation, and involves significant discomfort to the patient.

As a result of the foregoing drawbacks, techniques have been developed that permit coronary bypass grafting to be performed endoscopically, i.e., using elongated instruments inserted through incisions located between the ribs. A drawback of these keyhole techniques, however, is that they can be used only for coronary arteries that are readily accessible, and not, for example, those located posteriorly.

Alternatively, techniques such as percutaneous transluminal angioplasty ("PTA") have been developed for reopening arteries, such as the coronary arteries, that have become constricted by plaque. In these techniques, a balloon catheter typically is inserted into the stenosis and then inflated to compress and crack the plaque lining the vessel, thereby restoring patency to the vessel. Additionally, a vascular prosthesis, commonly referred to as a "stent," may be inserted transluminally and expanded within the vessel after the angioplasty procedure, to maintain the patency of the vessel after the PTA procedure.

The above-described techniques are useful only where the stenosis is localized, so that the bypass graft or PTA procedure, when completed, restores near-normal blood flow to the affected areas. For certain conditions, however, such as diffuse atherosclerosis, blockages may exist throughout much of the coronary artery system. In such situations, treatment, if possible, typically involves heart transplant.

U.S. Pat. No. 5,824,071 to Nelson et al. describes a retroperfusion technique in which one or more passageways or conduits are formed between the left ventricle and the coronary venous vasculature to supply retrograde perfusion of the myocardium. That patent discloses a valve that vents excess blood from the venous system to retain the pressure in the venous system less than a predetermined value.

Researchers also have proposed transfemoral coronary sinus balloon occlusion to treat patients with angina pectoris (Franz et al., "Transfemoral Balloon Occlusion of the Coronary Sinus in Patients with Angina Pectoris," *Radiologia Diagnostica*, 31 (1):35–41 (1990)). Pressure-controlled intermittent coronary sinus occlusion (PICSO) is a retrograde process that intermittently occludes the coronary sinus to re-direct venous blood to the ischemic myocardium.

U.S. Pat. No. 4,934,996 to Mohl et al. describes PICSO apparatus that includes an inflatable balloon disposed on the end of a catheter, a pump and control circuitry. The distal end of the balloon catheter is inserted percutaneously or intraoperatively into the coronary sinus. The control circuitry issues a trigger signal that turns the pump on and inflates the balloon to occlude the coronary sinus. During occlusion, blood pressure in the coronary sinus increases, and blood draining into the coronary sinus through healthy heart tissue is forced back into ischemic tissue.

Mohl et al. disclose that during occlusion, pressure in the coronary sinus reaches a plateau, and that continuing to occlude the coronary sinus once the plateau is reached could damage healthy heart tissue. According, the control circuitry estimates the plateau level of the coronary sinus pressure during each occlusion, and interrupts the occlusion based on the estimate. Such previously known PICSO apparatus is cumbersome and expensive due to the complex pump and control system.

Other researchers have hypothesized that continuously partially occluding the coronary sinus may provide beneficial retroperfusion of ischemic tissue. Previously known occlusion catheters, however, have not been designed to limit venous system pressures and cost-effectively achieve this goal.

It therefore would be desirable to provide simple apparatus and methods for continuously occluding all or a portion of a patient's venous vasculature, but without requiring an external pump and complex control circuitry.

It also would be desirable to provide apparatus and methods for continuously occluding all or a portion of a patient's venous vasculature, but which controls pressure in the occluded vasculature so that a selected pressure parameter does not exceed a predetermined level.

It further would be desirable to provide apparatus and methods for continuously occluding all or a portion of a patient's venous vasculature and provides an adjustable degree of occlusion, so that a selected pressure parameter does not exceed an adjustable predetermined level.

SUMMARY OF THE INVENTION

In view of the foregoing, it is an object of the present invention to provide apparatus and methods for continuously occluding all or a portion of a patient's venous vasculature to perfuse ischemic myocardium, but without requiring an external pump and complex control circuitry.

It is another object of this invention to provide apparatus and methods for continuously occluding all or a portion of a patient's venous vasculature, but which controls pressure in the occluded vasculature so that a selected pressure parameter does not exceed a predetermined level.

It is a further object of the present invention to provide apparatus and methods for continuously occluding all or a portion of a patient's venous vasculature and provides an adjustable degree of occlusion, so that a selected pressure parameter does not exceed an adjustable predetermined level.

These and other objects of the invention are accomplished by providing a tubular member having an end region adapted to be disposed in a portion of a patient's venous vasculature, e.g., the coronary sinus or great cardiac vein. The end region includes a lumen and a valve disposed proximal of the occlusion element and in communication with the lumen. An occlusion element optionally may be disposed in the end region that retains the tubular member within the patient's venous vasculature and occludes the flow of blood around the lumen. Alternatively, the end region may be sized so that its diameter occludes the venous vasculature when urged into engagement with the walls of the lumen.

The valve controls pressure within the occluded portion of the vasculature by venting excess blood proximal of the occlusion element via the valve. The valve is preferably a slit valve, although other types of valve mechanisms, such as a duck bill valve, may be employed. Optionally, more than one valve may be provided, so that the degree of venting may be adjusted in-situ to suit a particular patient's needs.

In a preferred embodiment, the tubular member forms an integral end of an elongated catheter adapted for percutaneous insertion. The catheter includes a proximal end that extends out of the patient's body, and includes a hemostatic valve through which therapeutic substances, e.g., drugs or other treatment fluids, may be injected into the patient's venous system, or through which blood may be periodically drawn, e.g., to analyze metabolites. The distal end region also may include an expandable member for regulating the pressure developed in the patient's vasculature. As a further alternative, the tubular member may comprise a separate member which may be percutaneously deployed.

Methods of using the apparatus of the present invention to provide acute or chronic perfusion of ischemic myocardium also are provided.

BRIEF DESCRIPTION OF THE DRAWINGS

Further features of the invention, its nature and various advantages will be more apparent from the accompanying drawings and the following detailed description of the preferred embodiments, wherein:

FIG. 3 is a side view of a portion of a human heart, partly in cross-section, illustrating placement of the apparatus of FIGS. 1;

FIG. 4 is a side view of a portion of a human heart, partly in section, illustrating placement of the apparatus of FIG. 2;

FIGS. 5A and 5B are, respectively, a side view of an alternative embodiment of an illustrative catheter of the present invention, and a partial sectional view of the distal end region;

FIG. 8 is a side view of a further alternative embodiment of an illustrative catheter of the present invention;

FIGS. 9A and 9B are, respectively, a detailed view of the end region of the catheter of FIG. 8 and a cross-sectional view of the end region of FIG. 9A; and FIG. 10 illustrates a method of engaging the end region of the catheter of FIG. 8 in a vessel.

DETAILED DESCRIPTION OF THE INVENTION

The present invention provides apparatus for continuously occluding a portion of a patient's venous vasculature, and methods of using that device to provide enhanced myocardial perfusion while limiting the pressure attained in the occluded portion of vasculature. More particularly, a device constructed in accordance with principles of the present invention comprises a catheter having an end region adapted to be disposed in a portion of a patient's venous vasculature, such as the coronary sinus or great cardiac vein. The end region includes a lumen and one or more valves for venting blood through the lumen proximal to regulate the pressure attained in the occluded portion of the vasculature. An occlusion element preferably is included in the end region to occlude flow around the lumen and retains the tubular member in place. Alternatively, the end region may be sized so that its exterior surface sealingly engages the interior surface of a vessel when urged therein.

A proximal end of the catheter includes a hemostatic valve that may be used to inject therapeutic substances into the patient's venous system. A distal end region also may include an expandable member that provides perfusion during diastole as well as systole. In an alternative embodiment of apparatus of the present invention, the device may comprise a separate unit that is affixed to the end of an elongated catheter for percutaneous placement, after which the catheter may be withdrawn, leaving the device in place.

Figure 1A:
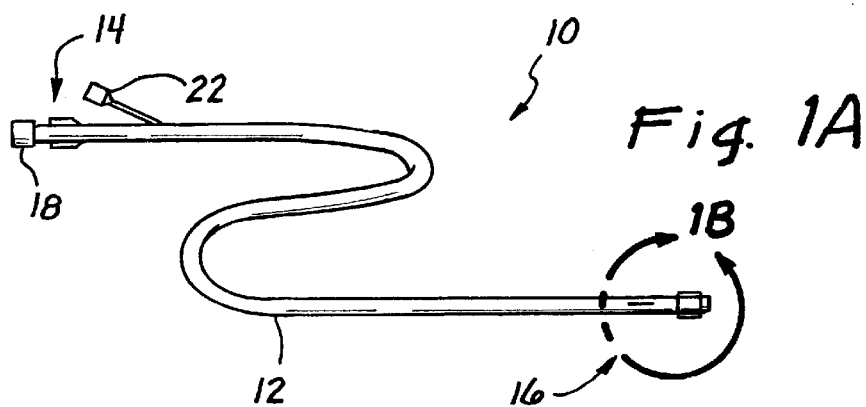
FIGS. 1A–1C are, respectively, a side view of an illustrative catheter of the present invention, a partial sectional view of the distal end region, and a perspective view of a support structure.
Figure 1B:
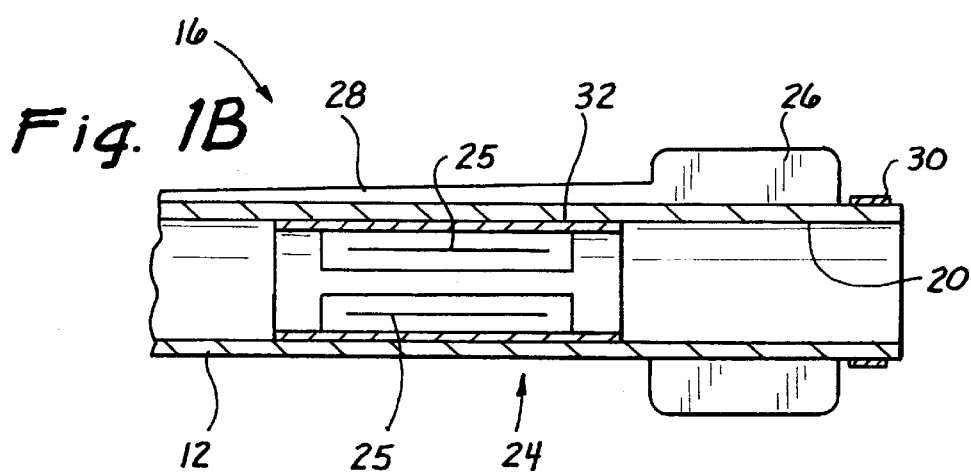
Figure 1C:
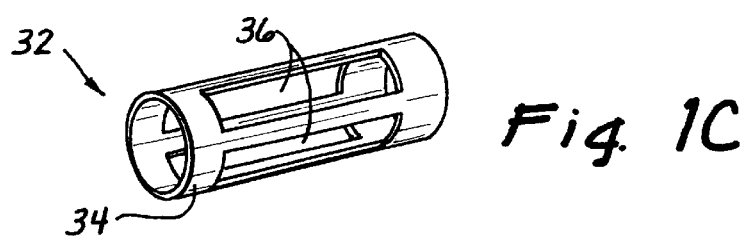

Referring now to FIGS. 1A–1C, a first illustrative embodiment of apparatus constructed in accordance with the principles of the present invention is described. Device 10 comprises catheter 12 having proximal end 14 and distal end region 16. Catheter 12 preferably comprises a biocompatible, flexible material typically used in catheters, for example, polyvinyl chloride, polyethylene, silicone, polyurethane, or combinations thereof. Proximal end 14 includes hemostatic valve 18, e.g., a Touhey-Borst valve, that permits a guide wire to be extended through lumen 20 of catheter 12, and inflation port 22. Distal end region 16 includes slit valve 24 and occlusion element 26, illustratively a balloon coupled to inflation port 22 by lumen 28.

Lumen 20 extends from proximal end 14 to distal end region 16 of catheter 12 to permit therapeutic substances, such as drugs, bioactive agents, angiogenic growth factors, free radical scavengers, saline, etc., to be introduced into the patient's venous system via hemostatic valve 18 (or to permit blood to be withdrawn). Occlusion element 26 occludes the flow of blood through the venous vasculature around the exterior of catheter 12, and also anchors distal end region 16 at a selected location of the patient's venous vasculature. Alternatively, instead of an inflatable member, occlusion element 26 may comprise an expandable sponge or elastomeric plug, ribs, barbs or flanges. As further described below with respect to the embodiment of FIG. 8, occlusion element 26 may be omitted entirely, and distal end region 16 of catheter 12 sized to sealingly engage the interior walls of the targeted venous vessel.

Distal end region 16 also may include radio-opaque marker ring 30, for example, a gold film, disposed on external surface of distal end region 16. Marker ring 30 enables the location of distal end region 16 to be determined using a fluoroscope. Alternatively, catheter 12 may include a radio-opaque material embedded within its walls, so that the entire catheter is visible under a fluoroscope.

Slit valve 24 comprises a series of circumferentially spaced-apart through-wall slits 25, for example, four slits spaced apart 90°. When the pressure within lumen 20 exceeds a first predetermined pressure, the wall segments between slits 25 bulge outward, thereby permitting blood to flow through the slits. When the pressure falls below a second predetermined pressure (which may be the same as the first pressure) the segments close towards one another, thereby preventing further fluid from escaping through the slits.

Because slits 25 structurally weaken the wall of catheter 12, flexing of catheter 12 may cause slit valve 24 inadvertently to open. Accordingly, to strengthen the wall of catheter 12 in the region of slits 25, support structure 32 is illustratively affixed either to the inner surface of the catheter 12. Alternatively, support structure 32 may be disposed on the exterior of catheter 12, or may be embedded within the wall of the catheter.

As depicted in FIG. 1C, support structure 32 comprises, for example, tubular member 34 having a plurality of elongated slots 36 formed along a mid-portion of the length of the tubular member, e.g., by laser cutting. Support structure 32 is disposed in catheter 12 so that each slit 25 is aligned with a corresponding one of plurality of elongated slots 36. Alternatively, support structure may be formed by welding a plurality of struts at either end to a hoop.

Referring still to FIGS. 1A–1C, the material of catheter 12, and the size, number and spacing of slits 25 may be selected so that the wall segments between slits 25 bulge outward only when the pressure within lumen 20 exceeds a first predetermined pressure, thereby permitting some of the blood to be vented proximally of occlusion element 26. For example, some researchers have suggested that the coronary venous system is susceptible to edema at pressures above 40 mm Hg. Accordingly, slit valve 24 may be configured to permit blood to be vented into through slits 25 when the pressure within lumen 20 exceeds 40 mm Hg.

Additionally, the material of catheter 12, and the size, number and spacing of slits 25 may be selected so that the wall segments between slits 25 re-seal only when the pressure within lumen 20 falls below a second predetermined pressure, thereby preventing further venting of blood into the right atrium. For example, it may be beneficial to maintain a minimum pressure in the coronary sinus of 30 mm Hg. Accordingly, slit valve 24 may be configured so that slits 25 re-seal when the pressure within lumen 20 falls below 30 mm Hg.

Figure 2:
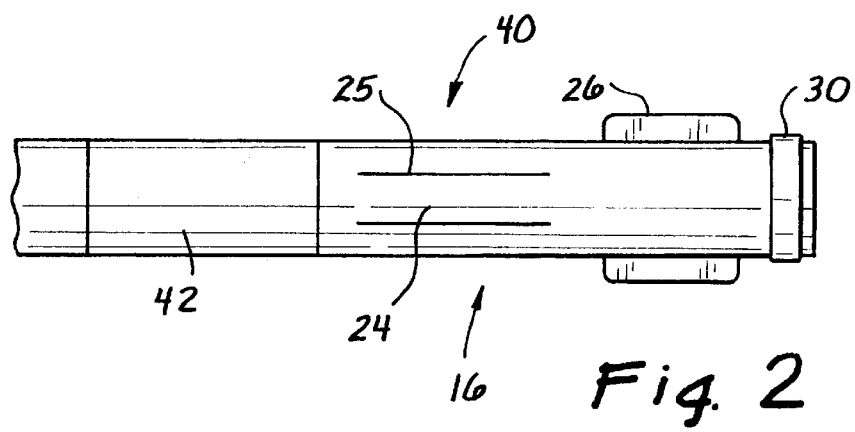
FIG. 2 is a side view of a distal end region of an alternative embodiment of the catheter of the present invention.

FIG. 2 illustrates an alternative embodiment of the device of the present invention, in which like parts are indicated by like numbers. Catheter 40 includes expandable section 42 disposed in end region 16 proximal to valve 24. Expandable section 42 may comprise, for example, a thin-walled portion of catheter 40, or a separately formed section comprising a different material. Expandable section 42 accumulates blood flowing into lumen 20 during systole, and contracts slightly during diastole to maintain the pressure applied to the occluded portion of the patient's vasculature, as described in detail hereinafter.

Referring now FIG. 3, use and operation of device 10 in accordance with the principles of the present invention is illustratively described for occluding a patient's coronary sinus. Distal end region 16 is illustratively shown placed in the coronary sinus using either a percutaneous or intraoperative approach. In an intraoperative method of installing device 10, right atrium RA or the superior vena cava first is exposed, and an opening is made with a trocar or scalpel. A guidewire (not shown) then is inserted until its distal end is inserted through coronary ostium CO and into coronary sinus CS. Catheter 12 is advanced along the guidewire until distal end 16 is inserted through coronary ostium CO.

Occlusion element 26 then is deployed, for example, by injecting an inflation medium, such as saline, into occlusion element 26 via inflation port 22. Inflation of occlusion element 26 not only anchors the distal end of catheter 12 in coronary sinus CO, but prevents blood draining into the coronary sinus from exiting through the coronary ostium into the right atrium. Thus, blood that normally would flow from the coronary sinus into right atrium RA instead accumulates in lumen 20 (this flow is illustrated by arrows AA), causing the pressure within lumen 20 and the rest of the venous vasculature to rise. This in turn forces blood draining into coronary sinus CS through healthy heart tissue to be forced back into ischemic tissue in heart H.

Eventually, the pressure in the patient's venous system and lumen 20 causes the wall segments between slits 25 to bulge outward until a first predetermined pressure (e.g., 40 mm Hg) is exceeded, at which point valve 24 opens. This permits some venous blood to be vented into right atrium RA (illustrated by arrows BB). After the wall segments between slits 25 bulge outward for a period of time, the pressure inside lumen 20 and the venous system decreases, permitting washout of blood in ischemic tissue. Valve 24 remains open until the pressure falls below a second predetermined pressure (e.g., 20 mm Hg), and blood begins to accumulate in lumen 20 again, repeating the foregoing cycle.

It should of course be understood that distal end region 16 may be lodged in a portion of the patient's coronary venous vasculature other than the coronary sinus, as needed to address a smaller portion of ischemic myocardium. For example, end region 16 may be disposed in the great cardiac vein. In this case, occlusion element 26 will effectively divide the venous system into a higher pressure region, distal to the occlusion element, and a lower pressure region, proximal of the occlusion element. Accordingly, when valve 24 opens, it vents excess blood to the lower pressure region through lumen 20 and valve 24, proximal to occlusion element 26.

In FIG. 4, the alternative embodiment of FIG. 2 is shown disposed in a patient's coronary sinus CS through coronary ostium CO. Expandable section 42 preferably comprises a soft balloon-like chamber that inflates at a third predetermined pressure, lower than the first and second predetermined pressures. When valve 24 is closed, expandable section 42 forms a reservoir that accumulates blood during systole, and maintains pressure in the venous system during diastole. When valve 24 opens, expandable section 42 also urges blood out of lumen 20 until the pressure in lumen 20 falls below the second predetermined pressure.

Referring now to FIGS. 5A and 5B, a further alternative embodiment of the device of the present invention is described. Device 50 comprises catheter 52 having proximal end 53 and distal end region 54 disposed within outer sheath 55. Catheter 52 includes a central lumen, hemostatic valve 56 at proximal end 53, and valves 57a–57c and occlusion element 58 in distal end region 54. Occlusion element 58 comprises, for example, a sponge-like foam that swells when exposed to blood for a predetermined interval. Catheter 52 is constructed as described hereinabove with respect to the embodiment of FIGS. 1, except that it includes multiple valves 57a–57c having different opening pressures. Outer sheath 55 is coupled to handle 59 that includes indicator window 60 indicating which of valves 57a–57c are exposed. Alternatively, sheath 55 may be disposed within the lumen of catheter 52 to selectively expose valves 57a–57c, and may in such an embodiment comprise a solid flexible member.

As shown in FIG. 5B, valves 57a–57c preferably are arranged so that the valve 57a, closest to the distal end, has the highest opening pressure, while valve 57c, closest to the proximal end, has the lowest opening pressure. Outer sheath 55 is configured to slide proximally and distally along catheter 52, as indicated by arrows A, to selectably uncover one or more of valves 57a–57c. Thus, once device 50 has been inserted in a portion of a patient's venous vasculature, outer sheath 55 may be moved in the proximal or distal directions to uncover slit valves 57a, 57a–57b or 57a–57c, to adjust the pressure attained with the venous system.

Illustratively, the central lumen of catheter 52 may be coupled through hemostatic valve 56 to a pressure monitor (not shown), and outer sheath 55 moved to adjust a measured pressure parameter, such as peak pressure or average pressure, to a desired value. Catheter 52 could then be disconnected from the pressure monitor, and outer sheath 55 locked in place.

Figure 6A:
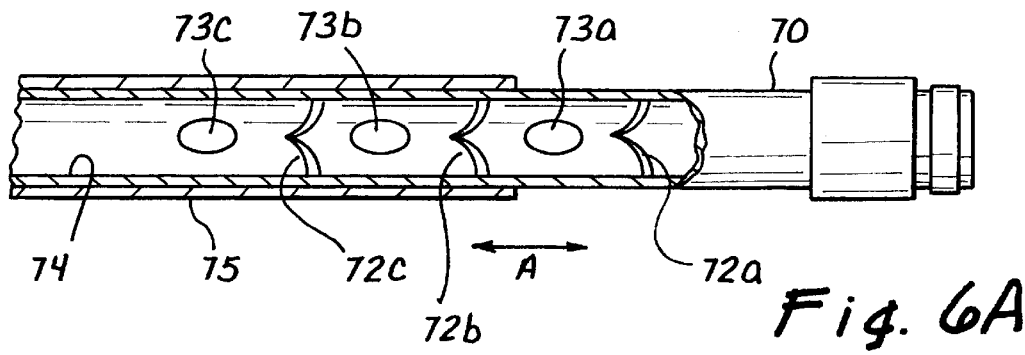
FIGS. 6A, 6B and 6C are, respectively, side views, partly in section, of a distal end region of another alternative embodiment of the catheter of the present invention depicting different pressure settings.
Figure 6B:
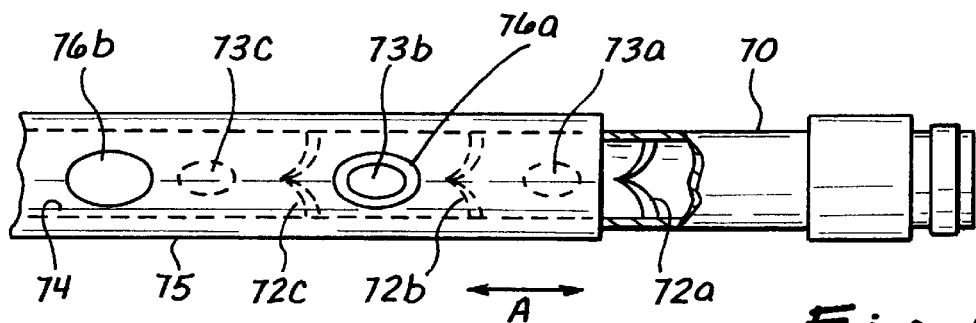
Figure 6C:
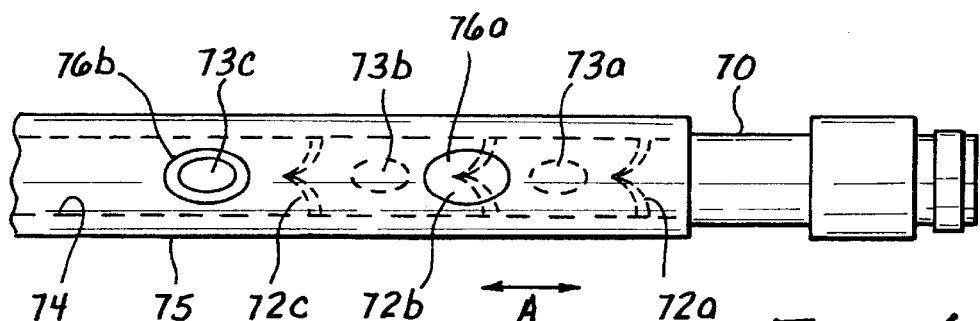

FIGS. 6A–6C depict an alternative embodiment of the device of FIG. 5, in which an outer sheath is selectively positioned relative to a valved catheter to attain a desired pressure in the venous system. Catheter 70 is similar in appearance to catheter 50 of FIG. 5, and is similarly constructed, except that slit valves 57a–57c are replaced by duck-bill valves 72a–72c and through-wall apertures 73a–73c, respectively. Valve 73a, closest to the distal end of catheter 70, has the highest opening pressure, while valve 73c, closest to the proximal end, has the lowest opening pressure. Thus, the portions of lumen 74 located proximally of each duck-bill valve define successively lower pressure regions when apertures 73a–73c are uncovered.

Outer sheath 75 is slidably disposed on catheter 70 and includes through-wall openings 76a and 76b. When outer sheath 75 is retracted to its proximal-most position, it blocks apertures 73b and 73c, so that blood exits only through valve 72a and aperture 73a. As depicted in FIG. 6B, outer sheath 75 may be moved in the distal direction so that opening 76a is aligned with aperture 73b, and apertures 73a and 73c are covered. In this position, blood exits only through aperture 73b and opening 76a, thereby providing an intermediate pressure level in the venous system. In FIG. 6C, outer sheath 75 is advanced to its distal-most position, at which opening 76b is aligned with aperture 73c, and apertures 73a and 73b are blocked. With outer sheath 75 in the position shown in FIG. 6C, blood exits only through apertures 73c and opening 76b, and the lowest pressure level is attained in catheter 70 and the venous vasculature. As will of course be understood, the valves of the embodiments of FIGS. 5 and 6 may be replaced with other suitable valve mechanisms and more or fewer valves may be employed to provide multiple selectable pressure levels.

Figure 7:
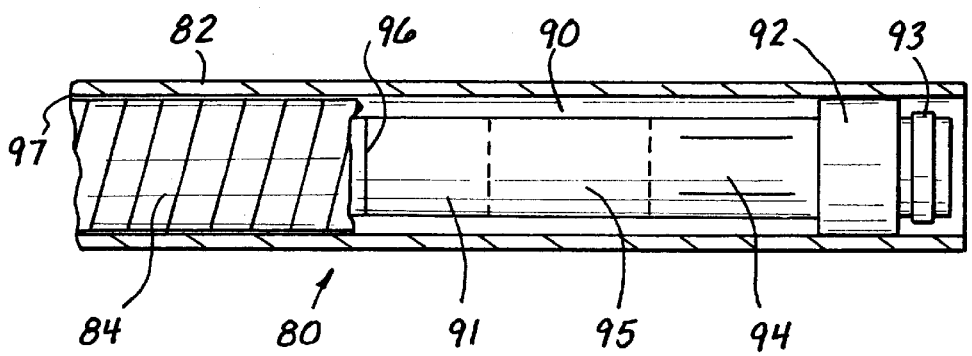
FIG. 7 is a side view, partly in section, of a still further alternative embodiment of apparatus of the present invention.

Referring now to FIG. 7, another alternative embodiment is described. Device 80 comprises introducer catheter 82, push tube 84, and occlusion device 90. Occlusion device 90 is similar in construction to distal end region 16 of the embodiment of FIGS. 1, and comprises tubular member 91 having an internal lumen, occlusion element 92, radiopaque marker band 93, slit valve 94 and expandable section 95. Occlusion device 90 further includes end cap 96 and pull wire 97. End cap 96 seals the proximal end of the internal lumen of member 91. Occlusion element 92 may comprise a detachable inflatable element, a sponge or foam plug, or an elastomeric ribs, barbs, etc., or simply a distal end of tubular member 91.

Occlusion device 90 is disposed in introducer catheter 82 so that end cap 96 seats against push tube 84 and pull wire 97 extends out of the proximal end of introducer catheter 82. Device 80 is adapted to be inserted percutaneously or intraoperatively through into the patients's right atrium, and then through the coronary ostium, into the coronary sinus or another part of the venous system. Once so positioned, for example, as determined using a fluoroscope, push tube 84 is held stationary while introducer catheter 82 is retracted proximally. This action causes occlusion device 90 to be deployed in the patient's venous system, permitting occlusion element 92 to engage the interior surface of the vein (or coronary sinus). Introducer catheter 82 and push tube 84 may then be withdrawn, leaving pull wire 97 extending out of the patient's body.

Operation of occlusion device 90 is as described for the distal end region of device 10 of FIGS. 1. If it is desired only to provide short-term transvenous myocardial perfusion, pull-wire 97 may be used to extract occlusion device 90 from the patient after treatment has been completed.

Referring now to FIGS. 8 to 10, a still further alternative embodiment of the device of the present invention is described. Device 100 comprises catheter 101 having proximal end 102 and distal end region 103 disposed. Catheter 101 includes central lumen 104 and valves 106a–106c in distal end region 103. Distal end region 103 has diameter D selected so as to sealingly engage and occlude a targeted portion of a vessel when urged therein (see FIG. 10). Catheter 107 includes hemostatic valve 105 on its proximal end, and is slidably disposed with lumen 104 of catheter 101 to selectively close-off valves 106a–106c from the interior of lumen 104. Wire braid 108 preferably is embedded within the wall of catheter 101 to reduce the imposition of bending stresses on valves 106a–106c, much like tubular member 34 of FIG. 1C.

Catheter 102, like the embodiment of FIGS. 5, preferably includes multiple valves 106a–106c having different opening pressures. As in the embodiment of FIGS. 5, valves 106a–106c preferably are arranged so that the valve 106a, closest to the distal end, has the highest opening pressure, while valve 106c, closest to the proximal end, has the lowest opening pressure.

Valves 106a–106c are a type of slit valve and are formed, for example, by incising a catheter to create elongated U-shaped flaps. When the pressure within lumen 104 exceeds a predetermined opening pressure, the flap bends outwards (as shown in dotted line in FIG. 9A), thus permitting blood to escape. The opening pressure of slit valves 106–106c may be empirically determined, and will depend on such factors as the stiffness of the catheter material and the width and length of the U-shaped flaps.

In FIG. 9B, catheter 107 is shown disposed within lumen 104 of catheter 102 with its distal end 109 blocking valves 106b and 106c. Catheter 107 extends through handle 110, so that an indicator mark on catheter 107 is visible through window 111. The clinician may move catheter 107 in the proximal or distal directions to block more or fewer of valves 106a–106c from communicating with the interior of lumen 104. This in turn permits the pressure attained in lumen 104 to be adjusted after implantation of the device. Thus, once device 100 has been inserted in a portion of a patient's venous vasculature, catheter 107 may be moved in the proximal or distal directions to uncover slit valves 106a, 106a–106b or 106a–106c, to adjust the pressure attained with the venous system.

Similar to the preceding embodiments, lumen 112 of catheter 107 may be coupled through hemostatic valve 105 to a pressure monitor (not shown), and catheter 107 then may be moved to adjust a measured pressure parameter, such as peak pressure or average pressure, to a desired value. Catheter 101 could then be disconnected from the pressure monitor, and catheter 107 locked in place. Alternatively, drugs or other therapeutic agents, such as described hereinabove, may be injected into the venous system via hemostatic valve 105 and lumen 112.

With respect to FIG. 10, distal end region 103 is illustratively shown passing through coronary ostium CO and engaged in coronary sinus CS. In this embodiment. no separate occlusion element is provided. Instead, distal end region 103 is simply advanced into the coronary sinus until the outer diameter of catheter 101 engages the interior surface of the venous vessel. Advantageously, occlusion of the vessel proximally of the point of occlusion of the vessel may be achieved without the need for a separate occlusion element.

Although preferred illustrative embodiments of the invention are described above, it will be obvious to one skilled in the art that various changes and modifications may be made therein without departing from the invention and the appended claims are intended to cover all such changes and modifications which fall within the true spirit and scope of the invention.

What is claimed is:

1. A method of providing retrograde transvenous myocardial perfusion, the comprising:

providing a device comprising a tubular member having a distal portion adapted to be disposed in a patient's venous system, a proximal end having means for sealing the proximal end, a first valve which opens when pressure distal to the first valve exceeds a predetermined maximum pressure and an occlusion element located on said distal portion;

delivering the device into a portion of a patient's venous vasculature;

using the occlusion element to substantially block blood flow at a selected location within the patient's venous vasculature; and opening the first valve when the venous blood pressure distal to the valve exceeds the predetermined maximum pressure, thereby allowing blood to flow through the first valve in the direction of normal venous blood flow so long as the pressure distal to the first valve is in excess of the predetermined maximum pressure.

2. The method of claim 1 wherein the device further comprises an expandable member in communication with the lumen, the method further comprising contracting the expandable member to perfuse the portion of the patient's venous system during cardiac diastole.

3. The method of claim 1 wherein the means for sealing further comprises a hemostatic valve communicating with the lumen, the method further comprising injecting a therapeutic substance through the hemostatic valve and into the patient's venous system.

4. The method of claim 1 wherein the device further comprises one or more additional valves, and a sheath disposed relative to the one or more additional valves, the method further comprising:

moving the sheath relative to the one or more additional valves to adjust a value of a pressure related parameter.

5. The method of claim 4 wherein the tubular member comprises an elongated catheter, the method further comprising:

coupling the proximal end to a monitoring device to measure a pressure in the lumen; and moving the sheath relative to the one or more additional valves to adjust the value of the pressure measured by the monitoring device.

* * * * *